United States Patent
Crews et al.

(10) Patent No.: US 9,687,302 B2
(45) Date of Patent: Jun. 27, 2017

(54) SURGICAL INSTRUMENTS HAVING IMPROVED WEAR RESISTANCE, AND METHODS OF MAKING THE SAME

(71) Applicant: Intuitive Surgical Operations, Inc., Sunnyvale, CA (US)

(72) Inventors: Samuel T. Crews, Palomar Park, CA (US); Andrew Crews, San Jose, CA (US); Edward P. Donlon, San Jose, CA (US); Craig Gerbi, Half Moon Bay, CA (US); Kenneth L. Gong, San Jose, CA (US); Karnarnadakala D. Krishnanand, San Jose, CA (US); Peling Lee, Palo Alto, CA (US); Theodore W. Rogers, Alameda, CA (US); John Ryan Steger, Sunnyvale, CA (US); Charles E. Swinehart, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 394 days.

(21) Appl. No.: 14/149,535

(22) Filed: Jan. 7, 2014

(65) Prior Publication Data

US 2014/0194895 A1  Jul. 10, 2014

Related U.S. Application Data

(60) Provisional application No. 61/750,273, filed on Jan. 8, 2013.

(51) Int. Cl.
*A61B 17/00* (2006.01)
*A61B 19/00* (2006.01)
(Continued)

(52) U.S. Cl.
CPC ...... *A61B 19/2203* (2013.01); *A61B 17/3421* (2013.01); *A61B 34/30* (2016.02);
(Continued)

(58) Field of Classification Search
CPC ............ A61B 19/2203; A61B 17/3421; A61B 2017/2926; A61B 2017/00845; Y10T 29/49826
See application file for complete search history.

(56) References Cited

U.S. PATENT DOCUMENTS 5,425,743 A  6/1995  Nicholas
6,817,974 B2  11/2004  Cooper et al.
(Continued)

FOREIGN PATENT DOCUMENTS

WO  WO-0213700 A2  2/2002
WO  WO-2010111319 A1  9/2010
(Continued)

OTHER PUBLICATIONS

Custom 465® Stainless, Technical Datasheet [online], [retrieved on Dec. 4, 2012]. Retrieved from the Internet:< URL: http://cartech.ides.com/datasheetaspx?i=101&E=55&FMT=PRINT>.
(Continued)

*Primary Examiner* — Richard Chang
(74) *Attorney, Agent, or Firm* — Jones Robb, PLLC

(57) ABSTRACT

A surgical apparatus includes a cannula and a surgical instrument. The cannula includes a curved longitudinal axis along at least a portion of its length. The surgical instrument includes an elongated shaft having a distal end and a proximal end, and an end effector coupled to the distal end of the elongated shaft. At least a portion of the end effector is configured to contact an inner surface of the cannula during insertion of the surgical instrument into the curved cannula. A threshold galling stress between the portion of the
(Continued)

end effector and an inner surface of the curved cannula is at least 10,000 pounds per square inch.

12 Claims, 4 Drawing Sheets

(51) Int. Cl.
  *A61B 17/34* (2006.01)
  *A61B 34/30* (2016.01)
  *A61B 17/29* (2006.01)
(52) U.S. Cl.
  CPC ............ *A61B 2017/00845* (2013.01); *A61B 2017/2926* (2013.01); *Y10T 29/49826* (2015.01)

(56) References Cited

U.S. PATENT DOCUMENTS

| | | | |
|---|---|---|---|
| 8,551,115 B2 | 10/2013 | Steger et al. | |
| 8,840,588 B2* | 9/2014 | Clement | A61M 13/003 604/164.01 |
| 9,055,960 B2* | 6/2015 | Stoy | A61B 19/2203 |
| 2011/0071542 A1 | 3/2011 | Prisco et al. | |
| 2011/0238064 A1* | 9/2011 | Williams | A61B 19/2203 606/41 |
| 2011/0245805 A1 | 10/2011 | Swinehart et al. | |

FOREIGN PATENT DOCUMENTS

WO  WO-2011126877 A1  10/2011
WO  WO-2012145048 A1  10/2012

OTHER PUBLICATIONS

Gall-Tough® Stainless, UNS No. S20161, Technical Datasheet [online], [retrieved on Dec. 4, 2012]. Retrieved from the Internet< URL: http://cartech.ides.com/datasheetaspx?l=101&TAB=DV_DS &E=250&SKEY=101.7.3122>.

Gall-Tough® PLUS Stainless, UNS No. S21800/S20162, Technical Datasheet [online], [retrieved on Dec. 4, 2012]. Retrieved from the lnternet:< URL: http://cartech.ides.com/datasheetaspx?l=101 &TAB=DV_DS&E=249&SKEY=101.7.3122>.

Nitronic 60 Stainless Steel Bar and Wire (UNS-S21800), Product Data Bulletin, Jul. 2011, 34 pages.

Review of the Wear and Galling Characteristics of Stainless Steels, A Designers' Handbook Series, Apr. 1978, pp. 1-28.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Search Report and Written Opinion for Application No. PCT/US2014/010518, mailed on Apr. 3, 2014, 15 pages.

* cited by examiner

PROXIMAL ←——→ DISTAL

SURGICAL INSTRUMENTS HAVING IMPROVED WEAR RESISTANCE, AND METHODS OF MAKING THE SAME

This application claims the benefit of U.S. Provisional Application No. 61/750,273, filed Jan. 8, 2013, which is incorporated by reference herein in its entirety.

TECHNICAL FIELD

The present disclosure relates generally to surgical instruments and systems. More particularly, the present disclosure relates to surgical instruments and cannulas that have relatively high resistance to galling and wear, and methods of making the same.

BACKGROUND

Minimally invasive surgeries, whether performed as a teleoperated (robotic) procedure or manually, often involve delivering a surgical instrument through a cannula to a surgical site inside a patient's body. To reduce the size of incisions and/or permit advancement along small paths in a patient's body, it can be desirable to reduce the overall lateral dimensions (e.g., diameter) of both the cannula and the instrument. However, relative movement between the surgical instrument and the cannula may result in wear and damage to either or both of the surgical instrument and the cannula as the surgical instrument and cannula contact one another. In particular, galling may occur between the cannula and the surgical instrument, which may result in damage to the instrument and cannula. Further, galling can prevent the surgical instrument from moving along the cannula. Therefore, it may be desirable to provide a surgical system that improves resistance to wear and damage, particularly from galling.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical apparatus includes a cannula and a surgical instrument. The cannula includes a curved longitudinal axis along at least a portion of its length. The surgical instrument includes an elongated shaft having a distal end and a proximal end, and an end effector coupled to the distal end of the elongated shaft. At least a portion of the end effector is configured to contact an inner surface of the cannula during insertion of the surgical instrument into the curved cannula. A threshold galling stress between the portion of the end effector and an inner surface of the curved cannula is at least 10,000 pounds per square inch.

In accordance with at least one exemplary embodiment, a surgical instrument includes an end effector. At least a portion of the end effector is made of an austenitic stainless steel having a composition comprising, in weight percent: about 0.15% maximum carbon, about 4% to about 8.5% manganese, about 15% to about 21% chromium, about 4% to about 10% nickel, about 2.5% to about 4.5% silicon, about 0.05% to about 0.25% nitrogen, and balance iron.

In accordance with at least one exemplary embodiment, a method of making a surgical apparatus includes forming a cannula tube including a curved longitudinal axis along at least a portion of its length. The inner surface of the cannula tube is burnished with a material having a hardness greater than the metal of the cannula tube. A surgical instrument configured to be inserted within the curved cannula tube is provided. A threshold galling stress between a portion of the end effector and the inner surface of the curved cannula is at least 10,000 pounds per square inch. After the burnishing, the inner surface of the curved cannula tube exhibits a galling resistance that is greater than the outer surface of the curved cannula tube.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The teachings of the present invention can be readily understood by considering the following detailed description in conjunction with the accompanying drawings.

DETAILED DESCRIPTION

Reference will now be made in detail to embodiments of the present disclosure, examples of which are illustrated in the accompanying drawings. One skilled in the art would readily recognize from the following description that alternative embodiments exist without departing from the general principles of the present disclosure. This description and the accompanying drawings illustrate exemplary embodiments and should not be taken as limiting, with the claims defining the scope of the present teachings. Various mechanical, compositional, structural, electrical, and operational changes may be made without departing from the scope of this description and the invention as claimed, including equivalents.

Exemplary embodiments described herein may be implemented using a da Vinci® Surgical System, commercialized by Intuitive Surgical, Inc. of Sunnyvale, Calif. An exemplary da Vinci® Surgical System is described in U.S. application Ser. No. 12/618,583, filed Nov. 13, 2009, published as U.S. Pub. No. 2011/0071542 on Mar. 24, 2011, which is incorporated herein by reference in its entirety. Knowledgeable persons will understand, however, that inventive aspects disclosed herein may be embodied and implemented in various ways, including teleoperated and non-teleoperated embodiments and implementations. Implementations on da Vinci® Surgical Systems are merely exemplary and are not to be considered as limiting the scope of the inventive aspects disclosed herein. For instance, exemplary embodiments described herein may be implemented by a teleoperated surgical system configured to utilize one or more surgical instruments through a single opening in a patient's body, such as through a single incision or port, or through multiple such openings. In addition, exemplary embodiments described herein may be implemented with a manual laparoscopic device instead of a teleoperated surgical system.

Figure 1:
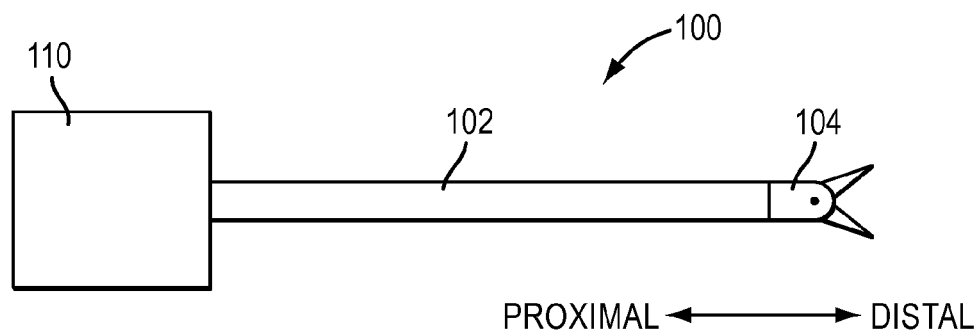
FIG. 1 is a side view of a surgical instrument, according to an exemplary embodiment.

Turning to FIG. 1, a side view of an exemplary embodiment of a surgical instrument 100 is shown. Surgical instrument 100 may be a teleoperated surgical instrument configured for use in a teleoperated surgical system. As shown in the exemplary embodiment of FIG. 1, surgical instrument 100 may include a shaft 102 and an end effector 104. Surgical instrument 100, including shaft 102 and end effector 104, and teleoperated surgical systems may be configured according the embodiments described in U.S. application Ser. No. 12/618,583, published as U.S. Pub. No. 2011/0071542 on Mar. 24, 2011. A wrist to provide one or more end effector DOF's (e.g., pitch, yaw; see e.g., U.S. Pat. No. 6,817,974 (filed Jun. 28, 2002) (disclosing surgical tool having positively positionable tendon-actuated multi-disk wrist joint), which is incorporated herein by reference) is optional and is not shown.

Shaft 102 may be a flexible shaft to permit the shaft 102 to bend according to one or more forces applied to shaft 102. For instance, shaft 102 may be passively flexible so that shaft 102 may bend according to an external force applied to shaft 102. For example, if surgical instrument 100 is inserted within a curved cannula with a passively flexible shaft 102, shaft 102 may bend as the shaft 102 passes through the curved inner wall of the cannula and is subjected to a force applied by the inner wall of the cannula. Shaft 102 may include a plurality of sections having different degrees of flexibility or stiffness, such as having sections of relatively high flexibility to reduce friction with an inner wall of a cannula and sections of relatively low flexibility to provide support and buckling resistance. In addition, shaft 102 is not limited to being passively flexible but instead one or more portions of shaft 102 may be actively flexible. According to an exemplary embodiment, shaft 102 may be configured according to the exemplary embodiments of U.S. Pat. No. 8,551,115, entitled "Curved Cannula Instrument," issued Oct. 8, 2013, which is hereby incorporated by reference in its entirety.

End effector 104 is generally configured to perform one or more surgical procedures including, but not limited to, for example, tissue cutting, tissue grasping, tissue sealing, tissue connection, and tissue ablation. End effector 104 may be a device configured to perform any of these surgical procedures. For instance, end effector 104 may be a dissector, a curved scissor, a scalpel, a spatula, a probe, a clip applier, a cautery hook, forceps, a sealer, or a combination thereof. As shown in the exemplary embodiment of FIG. 1, end effector 104 may be located at a distal end of shaft 102.

Surgical instrument 100 may include a force transmission mechanism 110. Force transmission mechanism 110 may be configured to actuate surgical instrument 100 and may be configured according to the exemplary embodiments described in U.S. application Ser. No. 12/618,583, filed on Nov. 13, 2009, and published as U.S. Pub. No. 2011/0071542 on Mar. 24, 2011. For example, force transmission mechanism 110 may be configured to move or actuate end effector 104. For instance, if end effector 104 is configured grasp tissue, force transmission mechanism 110 may actuate end effector 104 to open and close. According to an exemplary embodiment, end effector 104 may be actuated via one or more force transmission members that extend from force transmission mechanism 110 along shaft 102 to end effector 104. In another example, force transmission mechanism 110 may rotate end effector 104, such as via rotation of shaft 102. As shown in the exemplary embodiment of FIG. 1, force transmission mechanism 110 may be located at a proximal end of shaft 102, with shaft 102 coupling force transmission mechanism 110 with the end effector 104.

Figure 2:
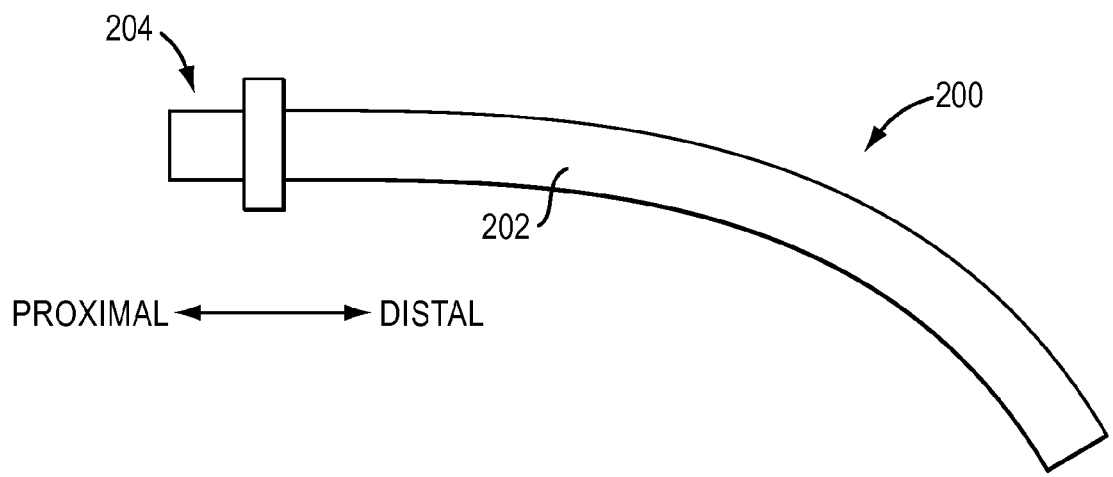
FIG. 2 is a side view of a cannula, according to an exemplary embodiment.

Turning to FIG. 2, an exemplary embodiment of a curved cannula 200 is shown. Curved cannula 200 may be configured according to the exemplary embodiments described in U.S. application Ser. No. 12/618,583, filed on Nov. 13, 2009, and published as U.S. Pub. No. 2011/0071542 on Mar. 24, 2011. According to an exemplary embodiment, curved cannula 200 may include at least a curved portion and may include one or more straight portions, such as proximal and distal to a the curved portion. According to an embodiment, curved cannula 200 may be rigid. As a result, when a passively flexible surgical instrument is inserted within curved cannula 200, the wall 202 of curved cannula 200 may exert a force upon the passively flexible surgical instrument and cause the surgical instrument to bend.

Cannula 200 may have a transverse cross-section that is rounded. For example the cross-section may be circular or near-circular. Alternatively, the curved section may have an oval cross section, and the oval is oriented such that a major axis of the oval can be generally aligned with the bend radius of the curved portion of the cannula. The oval cross-section increases the contact area between the inner wall of the cannula and the end effector, lowering the contact stress and the possibility for galling. Examples of such cannulas have been disclosed in U.S. Patent Application Publication 2011/0245805, filed May 14, 2010, which is incorporated herein by reference.

Curved cannula 200 may include a mounting section 204 configured to couple with a teleoperated surgical system, such as a patient manipulator of a teleoperated surgical system, as described in the exemplary embodiments of U.S. application Ser. No. 12/618,583, filed on Nov. 13, 2009, and published as U.S. Pub. No. 2011/0071542 on Mar. 24, 2011. For instance, as shown in the exemplary embodiment of FIG. 3, a curved cannula 310 may be mounted to a patient side manipulator (PSM) 300. PSM 300 may support and move a combination of curved cannula 300 and a surgical instrument 312. As depicted in the exemplary embodiment of FIG. 3, surgical instrument 312 may include a force transmission mechanism 314, a passively flexible shaft 316, and an end effector 318. Instrument 312 may be mounted on an instrument actuation interface assembly 301 of PSM 300. Interface discs 315 may couple actuation forces from servo actuators in PSM 300 to move instrument 312 components. Instrument 312 may include a wrist (not shown) to provide one or more end effector DOF's (e.g., pitch, yaw; see e.g., U.S. Pat. No. 6,817,974 (filed Jun. 28, 2002) (disclosing surgical instrument having positively positionable tendon-actuated multi-disk wrist joint), which is incorporated herein by reference.

Figure 3:
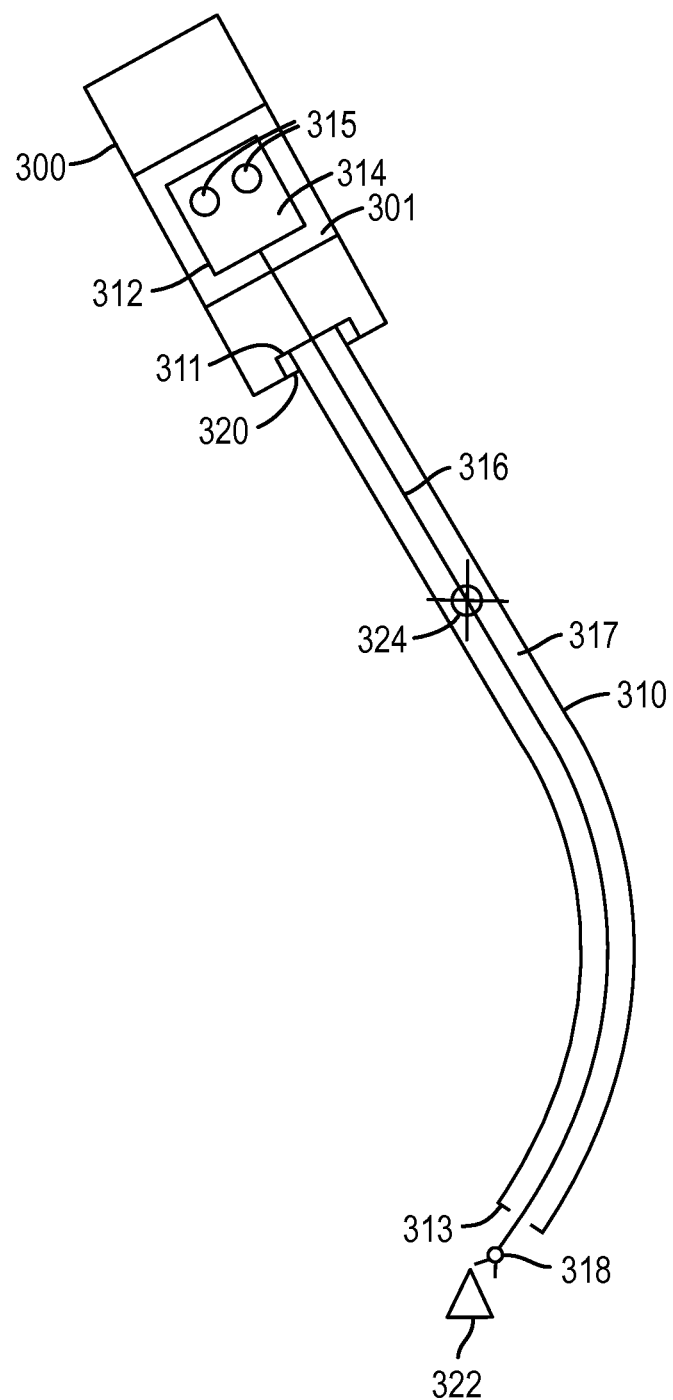
FIG. 3 is a schematic view of a portion of a patient side manipulator that supports and moves a combination of a curved cannula and a surgical instrument, according to an exemplary embodiment.

As shown in the exemplary embodiment of FIG. 3, curved cannula 310 has a proximal end 311, a distal end 313, and a central channel 317 that extends between proximal end 311 and distal end 313. According to an exemplary embodiment, curved cannula 310 may be a rigid, single piece cannula. As depicted in the exemplary embodiment of FIG. 3, proximal end 311 of curved cannula 310 is mounted to a mount 320 of PSM 300.

During use, the flexible shaft 316 of instrument 312 may extend through the central channel 317 of curved cannula so that a distal portion of flexible shaft 316 and end effector 318 extend beyond the distal end 313 of cannula 310 in order to reach a surgical site 322. Instrument 312 and curved cannula 310 may move in pitch and yaw motions around a remote center of motion 324 located along cannula 310, which is typically placed at an incision in the patient's body wall.

As discussed in U.S. application Ser. No. 12/618,583, filed on Nov. 13, 2009, and published as U.S. Pub. No. 2011/0071542 on Mar. 24, 2011, curved cannulas may advantageously provide improved triangulation for surgical instruments. As a result, a surgical site 322 may be relatively unobstructed the field of view of an endoscope (not shown) and fewer incisions or port may be used to access the surgical site 322. For instance, a single incision or port may be used for a plurality of cannulas and instruments instead of, for example, an incision or port for each cannula and instrument combination.

Figure 4:
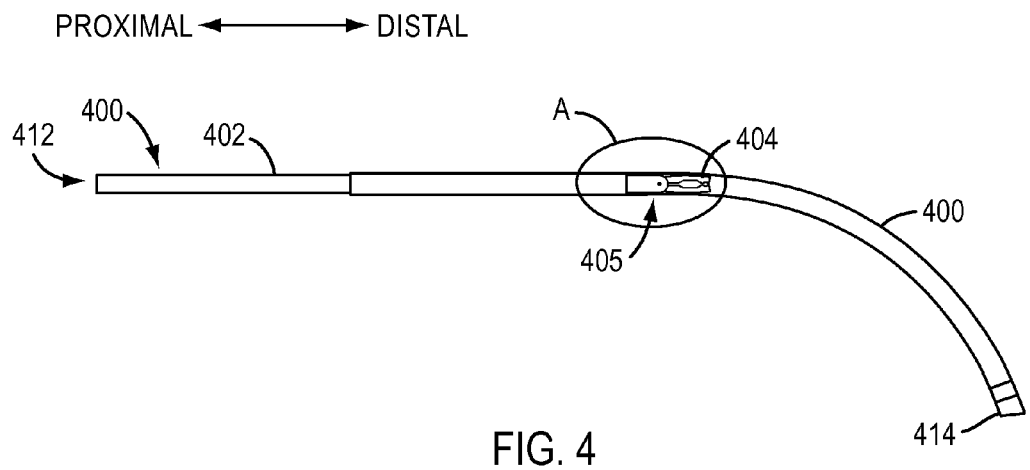
FIG. 4 is a side cross-sectional view of a cannula and surgical instrument inserted within the cannula, according to an exemplary embodiment.

A surgical instrument may include a flexible shaft to permit the surgical instrument to be inserted within a curved cannula and travel along the curvature of the curved cannula. However, relative movement between a surgical instrument and a curved cannula may cause contact between the instrument and the cannula. Turning to FIG. 4, an exemplary embodiment of a surgical instrument 400 and a curved cannula 410 is shown. Surgical instrument 400 includes an elongated shaft 402 having an end effector 404 coupled to a distal end 405 of shaft 402. Cannula 410 includes a tube having at least a curved portion, the tube having a proximal end 412 and a distal end 414.

Although, the physical dimensions of a cannula 410 and an end effector 404 may permit end effector 404 to pass within an interior of cannula 410, the physical structures and geometries of cannula 410 and end effector 404 may result in contact between cannula 410 and end effector 404 when end effector 404 passes through the interior of cannula 410. For instance, an end effector that is relatively large may in comparison to other end effectors may have a greater incidence of contact with an interior surface of a cannula, Further, although it may be desirable for the shaft 402 of surgical instrument 400 to be sufficiently flexible to permit instrument 400 to be inserted and withdrawn through the interior of cannula 410 with ease and so there is relatively little friction between instrument 400 and cannula 410, it may also be desirable for shaft 402 to be sufficiently rigid to support instrument 400 and end effector 404 and minimize or avoid buckling. Such rigidity can permit end effector 404 to be controlled with a relatively high degree of precision once the surgical instrument is advanced from the cannula 410 to perform a procedure at the surgical site. Thus, these countervailing considerations, besides the physical dimensions of a cannula 410 and a surgical instrument 400, may result in a surgical instrument 400 that contacts an inner wall of curved cannula 410 when surgical instrument 400 is actuated. For instance, contact may occur between surgical instrument 400 and cannula 410 when instrument 400 is inserted and withdrawn through curved cannula 410. Further, instrument 400 may be rotated within cannula 410, causing contact between instrument 400 and cannula 410.

Figure 5:
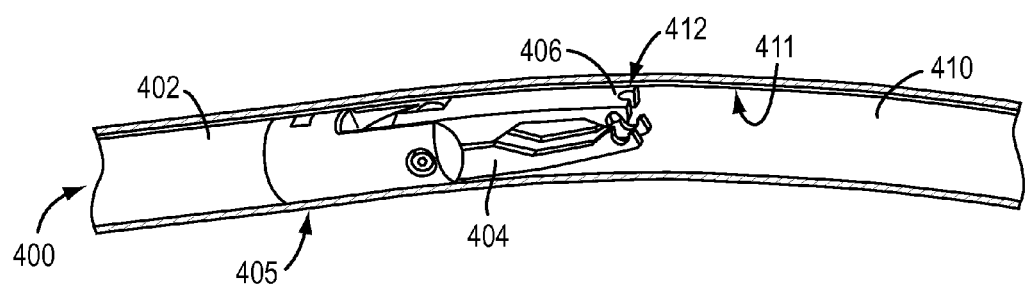
FIG. 5 is an enlarged view of area A of FIG. 4.

One area of contact between a surgical instrument and a cannula may be between the end effector of an instrument and the cannula. Although the shaft of a surgical instrument is flexible, as mentioned above, the shaft also has a degree of rigidity to support an end effector, which may press an end effector at a distal end of a surgical instrument against an interior wall of a cannula when the end effector traverses a curve of the cannula. Further, the end effector, or a portion of an end effector, may be made of a rigid material and end effectors may vary in size and shape. Turning to FIG. 5, an enlarged view of region A in FIG. 4 is shown. When relative movement occurs between instrument 400 and cannula 410, contact may occur between end effector 404 and a wall 411 of cannula 410.

For instance, a surface 406 of end effector 404 may contact an interior surface 412 of the wall 411 of cannula 410. Thus, the greatest degree of stress between surgical instrument 400 and curved cannula 410 may occur at surface 406 of end effector 404 and interior surface 412 of wall 411 of curved cannula 410. If the stress exceeds a threshold, wear and damage may occur to end effector 404 and/or cannula 410, such as at surfaces 406, 412. Further, wear of the instrument and/or cannula may even cause seizure of the instrument within the cannula.

One mode of wear and damage that may occur between surfaces is galling. Galling is a type of surface damage occurring between sliding surfaces, which may be characterized by microscopic roughening and the creation of protrusions above a surface. Metal surfaces, in particular, may exhibit galling damage when metal surfaces contact one another, such as via a sliding motion. For instance, when surfaces are pressed against one another, asperities or high points on the surfaces may come into contact with one another and become plastically deformed. This may lead to adhesion and material transfer between the surfaces, which may manifest as surface roughening and surface build-up or lump growth. Surface roughening may indicate locations where material has been removed. Surface build-up or lump growth have grown may indicate locations where material has been added. Further, galling may more easily occur between similar materials, although galling may occur between dissimilar materials as well.

One way to indicate whether two surfaces will experience galling is to determine a threshold galling stress. The threshold galling stress can be measured according to any testing methods that are accepted by those skilled in the art. For example, one galling test used in industry is the button and block test, which has been disclosed in "Review of the Wear and Galling Characteristics of Stainless Steels" published by the Committee of Stainless Steel Producers, American Iron and Steel Institute, April 1978. In the button and block test, two samples of material (which may be samples of the same material or different material) are placed in contact, with one sample being in the form of a button and the other sample being in the form of a block. A compressive stress is applied to the samples, such as to the button, and the samples are moved relative to one another, such as by rotating the button relative to the block. The compressive stress is removed and the mated surfaces of the two samples are visually inspected for galling. If no galling has occurred, new samples are tested but with a larger compressive stress. This procedure is repeated with increased compressive stress until galling occurs.

According to one definition, the threshold galling stress is the highest stress level at which galling does not occur. This definition is used when referring to threshold galling stress, unless stated otherwise. According to another definition, the threshold galling stress is the midpoint between the highest stress at which galling does not occur and the stress at which galling was first observed. The latter definition, for example, may be used when compressive stress is increased in relatively large increments. Further, because the threshold galling stress is determined by using two samples (i.e., button and block), the threshold galling stress is determined for the particular materials that the two samples are made of. In other words, threshold galling stress indicates the stress at which two particular materials will experience galling when those two materials rub against one another.

An individual material may be understood to have galling resistance because the material exhibits relatively high threshold galling stresses when paired with other materials. As a result, an individual material may be referred to as being "galling resistant" or "anti-galling."

In view of these considerations, it may be desirable to provide a surgical instrument and cannula for a teleoperated surgical system that exhibit a resistance to galling. A surgical instrument and curved cannula that are galling resistant would advantageously minimize or avoid surface damage that results from galling. This may enable the instrument and cannula to be used without potential risk of wear and/or damage. Also, such alloy resistance can provide better control of the system, preventing potential seizing of the surgical instrument as it is advanced through the cannula.

According to an exemplary embodiment, a galling resistant material may be used for at least one of a surgical instrument and a curved cannula so that a surgical apparatus including the surgical instrument and the curved cannula has a threshold galling stress between the surgical instrument and the cannula of at least 10,000 pounds per square inch (10 ksi). For instance, at least one of the surgical instrument and the curved cannula may be made of a galling resistant alloy that, when paired with the material of the other of the surgical instrument and the curved cannula, provides a threshold galling stress of at least 10 ksi.

In various exemplary embodiments, the end effector of the surgical instrument may be made of a galling resistant material. In particular, one or more portions of an end effector that are more susceptible to contact with an inner surface of a cannula may be made of a galling resistant material. For instance, because a surface 406 of the end effector 404 of a surgical instrument 400 may contact an interior surface 412 of a wall 411 of a curved cannula 410, as shown in FIG. 5, at least a portion of end effector 404 located at surface 406 may be made of a galling resistant material so that a threshold galling stress between end effector 404 and curved cannula 410 is at least 10 ksi, with respect to the material of curved cannula 410. More particularly, materials of end effector 404 and curved cannula 410 may be utilized so that a threshold galling stress between end effector 404 and curved cannula 410 is at least 10 ksi. According to an exemplary embodiment, an entirety of end effector 404 may be made of the same material as the portion of end effector 404 at surface 406. According to another exemplary embodiment, other portions of end effector 404 may be made of different materials than the portion of end effector 404 at surface 406.

According to an exemplary embodiment, a material of shaft 402 of surgical instrument 400 may be different from a material of end effector 404. Because the greatest stress may occur between end effector 404 and curved cannula 410, it may not be necessary to make shaft 402 out of a galling resistant material. Thus, at least a portion of end effector 404 may be made of a galling resistant material while shaft 402 is made from a different material than end effector 404 so that shaft may remain flexible, as described above.

If end effector 404 is made of a galling resistant material, curved cannula 410, such as wall 411 of curved cannula 410, may be made of a different material. According to an exemplary embodiment, curved cannula 410 may be made of a stainless steel. For instance, curved cannula 410 may be made of a martensitic stainless steel or a martensitic, age-hardenable stainless steel. One example of a martensitic, age-hardenable stainless steel for a curved cannula has a nominal composition, in weight percentage, about 0.02% max carbon, about 0.25% max silicon, about 10.75% to about 11.25% nickel, about 1.50% to about 1.80% titanium, about 0.25% max manganese, about 11.00% to about 12.50% chromium, about 0.75% to about 1.25% molybdenum, and balance iron. An exemplary alloy meeting this composition is Custom 465®, which is manufactured by Carpenter Technology Corporation. Other martensitic stainless steels, such as 410 stainless steel or 420 stainless steel, and other age-hardenable stainless steels, such as 17-4 stainless steel, may be used for a cannula, according to an exemplary embodiment.

A curved cannula and a surgical instrument may be configured so that a threshold galling stress between the curved cannula and the surgical instrument is at least 10,000 pounds per square inch (10 ksi). According to an exemplary embodiment, materials for the curved cannula and the surgical instrument may be selected so that the threshold galling stress between the curved cannula and the surgical instrument is at least 10 ksi.

When a curved cannula is made of a martensitic stainless steel, a surgical instrument may be made of a material to provide a threshold galling stress of at least 10 ksi between the surgical instrument and the martensitic stainless steel of the curved cannula. According to an exemplary embodiment, at least a portion of the surgical instrument may be made of an austenitic stainless steel, such as a fully austenitic stainless steel. In particular, at least a portion of an end effector of the surgical instrument may be made of an austenitic stainless steel, according to an exemplary embodiment. Thus, the austenitic stainless steel of the surgical instrument and the martensitic stainless steel of the curved cannula may provide a threshold galling stress of at least 10 ksi.

A surgical instrument and a curved cannula may be configured to provide even greater threshold galling stresses. According to an exemplary embodiment, the curved cannula and the surgical instrument may be made of materials to provide a threshold galling stress of at least 20,000 pounds per square inch (20 ksi). In a further exemplary embodiment, the curved cannula and the surgical instrument may be made of materials to provide a threshold galling stress of at least 50,000 pounds per square inch (50 ksi).

According to an exemplary embodiment, at least a portion of a surgical instrument may be made of an austenitic stainless steel having a composition of, in weight percent, about 0.15% maximum carbon, about 4% to about 8.5% manganese, about 15% to about 21% chromium, about 4% to about 10% nickel, about 2.5% to about 4.5% silicon, about 0.05% to about 0.25% nitrogen, and balance iron. The austenitic stainless steel main include additional elements and/or incidental impurities including one or more of, for example, in weight percent, about 0.040% maximum phosphorous, about 0.030% maximum sulfur, about 0.75% maximum copper, about 0.050% maximum titanium, about 0.020% maximum aluminum, about 0.0015% maximum boron, about 0.10% maximum niobium (also referred to as columbium), about 0.050% maximum tin, about 0.20% maximum vanadium, and about 0.15% maximum tungsten.

According to another exemplary embodiment, at least a portion of a surgical instrument may be made of an austenitic stainless steel having a composition of, in weight percent, about 0.15% maximum carbon, about 4% to about 8.5% manganese, about 15% to about 18% chromium, about 4% to about 8.5% nickel, about 3% to about 4.2% silicon, about 0.08% to about 0.20% nitrogen, and balance iron. This embodiment may include any combination of the additional elements and/or incidental impurities discussed in the previous embodiment.

According to another exemplary embodiment, at least a portion of a surgical instrument may be made of an austenitic stainless steel having a composition of, in weight percent, about 0.06% to about 0.08% carbon, about 7.50% to about 8.50% manganese, about 16.00% to about 17.00% chromium, about 8.00% to about 8.50% nickel, about 3.7% to about 4.20% silicon, about 0.10% to about 0.18% nitrogen, and balance iron. The austenitic stainless steel main include additional elements and/or incidental impurities including one or more of, for example, in weight percent, about 0.040% maximum phosphorous, about 0.030% maximum sulfur, about 0.75% maximum molybdenum, about 0.75% maximum copper, about 0.050% maximum titanium, about 0.020% maximum aluminum, about 0.0015% maximum boron, about 0.10% maximum niobium (also referred to as columbium), about 0.050% maximum tin, about 0.20% maximum vanadium, and about 0.15% maximum tungsten. An example of such a steel is Nitronic® 60, which is distributed by High Performance Alloys.

According to another exemplary embodiment, at least a portion of a surgical instrument may be made of an austenitic stainless steel having a composition of, in weight percent, about 0.15% maximum carbon, about 4.00% to about 6.00% manganese, about 15.00% to about 18.00% chromium, about 4.00% to about 6.00% nickel, about 3.00% to about 4.00% silicon, about 0.08% to about 0.20% nitrogen, and balance iron. The austenitic stainless steel main include additional elements and/or incidental impurities including one or more of, for example, in weight percent, about 0.040% maximum phosphorous and about 0.040% maximum sulfur. An example of such a steel is Gall-Tough® Stainless, which is manufactured by Carpenter Technology Corporation.

According to another exemplary embodiment, at least a portion of a surgical instrument may be made of an austenitic stainless steel having a composition of, in weight percent, about 0.15% maximum carbon, about 4.00% to about 8.00% manganese, about 16.50% to about 21.00% chromium, about 6.00% to about 10.00% nickel, about 2.50% to about 4.50% silicon, about 0.50% to about 2.50% molybdenum, about 0.05% to about 0.25% nitrogen, and balance iron. The austenitic stainless steel main include additional elements and/or incidental impurities including one or more of, for example, in weight percent, about 0.040% maximum phosphorous and about 0.040% maximum sulfur. An example of such a steel is Gall-Tough® Plus Stainless, which is manufactured by Carpenter Technology Corporation.

According to an exemplary embodiment, at least a portion of a surgical instrument may be made of other austenitic stainless steels, such as, for example, 304 stainless steel. Further, although at least a portion of a surgical instrument may be made of an austenitic stainless steel, as discussed above, materials for the surgical instrument are not limited to austenitic stainless steels. According to an exemplary embodiment, at least a portion of a surgical instrument may be made of a martensitic, age-hardenable stainless steel, such as, for example, Custom 465®, which is described above.

Although a portion of a surgical instrument may be made of an iron-based steel, as described in the exemplary embodiments above, metal portions of the surgical instrument may not be limited to iron-based alloys. According to another exemplary embodiment, at least a portion of a surgical instrument may be made of nickel-base alloy or a copper-base alloy. Such alloys may also exhibit a relatively high threshold galling stress when engaged with other materials.

A cannula and at least a portion of an instrument used together may each be made of materials described in the various exemplary embodiments herein. For example, a cannula may be made of, for example, Custom 465® alloy, and at least a portion of the instrument may be made of, for example, Nitronic® 60. In another example, a cannula may be made of, for example, 420 stainless steel, and at least a portion of the instrument may be made of, for example, 304 stainless steel. In another example, a cannula may be made of, for example, 420 stainless steel, and at least a portion of the instrument may be made of, for example, Custom 465® alloy. In another example, a cannula may be made of, for example, 17-4 stainless steel, and at least a portion of the instrument may be made of, for example, Custom 465® alloy. Other combinations of the materials described in the various embodiments herein are also contemplated.

According to an exemplary embodiment, a nickel-based alloy may have a composition of, for example, in weight percent, about 4% to about 8% tin, about 4% to about 4.5% bismuth, balance nickel. The nickel-based alloy may include additional elements and/or incidental impurities. For instance, a nickel-based alloy may have a composition of about 4% tin, about 1% maximum iron, about 4% to about 4.5% bismuth, about 12% chromium, about 2.5% molybdenum, and balance nickel. An example of such an alloy is Waukesha Metal® 88, which is distributed by Waukesha Foundry Company. In another instance, a nickel-based alloy may have a composition of about 8% tin, about 4% bismuth, about 7% zinc, about 2% manganese, and balance nickel. An example of such an alloy is Waukesha Metal® 23BI, which is distributed by Waukesha Foundry Company. In another instance, a nickel-based alloy may have a composition of about 8% tin, about 8% zinc, about 2% manganese, about 6% silver, and balance nickel. An example of such an alloy is Waukesha Metal® 54C, which is distributed by Waukesha Foundry Company.

According to an exemplary embodiment, a copper-based alloy may have a composition of, for example, in weight percent, about 3.5% to about 4.5% bismuth, about 20% nickel, and balance copper. The copper-based alloy may include additional elements and/or incidental impurities. For instance, a copper-based alloy may have a composition of about 4% tin, about 1% maximum iron, about 4.5 bismuth, about 20% nickel, about 4% zinc, and balance copper. An example of such an alloy is Waukesha Metal® 119, which is distributed by Waukesha Foundry Company. In another instance, a copper-based alloy may have a composition of about 3.5 bismuth, about 20% nickel, about 1% aluminum, about 20% zinc, about 20% manganese and balance copper. An example of such an alloy is Waukesha Metal® 126, which is distributed by Waukesha Foundry Company.

According to an exemplary embodiment, a curved cannula and an end effector of a surgical instrument may be made of different materials. However, although the galling resistant materials discussed in the embodiments above were in relation to a surgical instrument, such as the end effector or at least a portion of the end effector, the galling resistant materials may instead be used in the curved cannula. In addition, the embodiments herein are not limited to curved cannulas and end effectors of surgical instruments being made of different materials. According to an exemplary embodiment, an end effector of a surgical instrument and a curved cannula may be made of the same material. For instance, at least a curved section of a curved cannula may be made of the same material as a portion of an end effector that comes into contact with the curved cannula.

According to an exemplary embodiment, various sections of a curved cannula can be made of different materials. For example, a straight section located at a proximal end of a curved cannula is less likely to contact an end effector extending through it, and therefore is less likely to be galled. The straight section can be made of a metal that has a lower threshold galling stress in relation to the material of the end effector. On the other hand, the end effector may contact the curved section, so that galling is more likely to occur there. To address this, the curved section can be made of a galling-resistant metal that has a threshold galling stress of at least 10 ksi in relation to a material of surgical instrument. Different sections of a curved cannula can be connected together using any methods used in the art, such as, for example, welding.

According to an exemplary embodiment, a manufacturing process may be utilized to provide a surgical apparatus with enhanced galling resistance. A surgical instrument may be provided that includes at least a portion made of a material discussed in the embodiments above. For instance, the end effector or at least a portion of the end effector may be made of a material discussed in the embodiments above. Further, a curved cannula may be provided by, for example, welding sheet or strip metal into the form of a tube and forming the tube into a curved cannula tube. The tube may be further heat treated in one or more steps.

Figure 6:
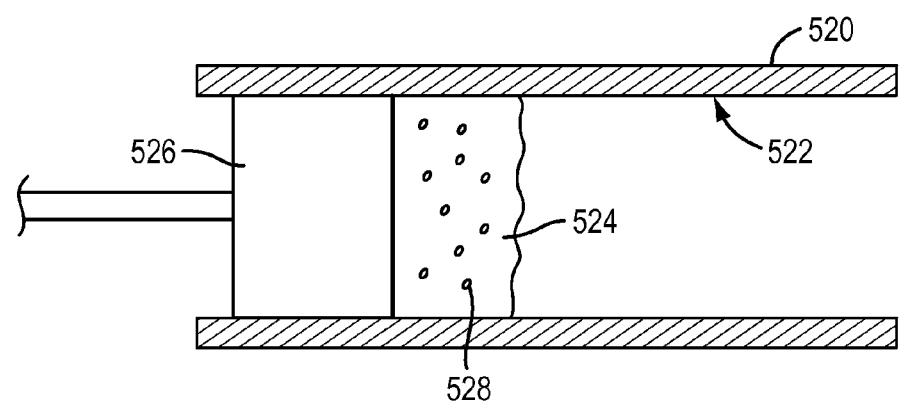
FIG. 6 is a side cross-sectional view of a polishing process for a cannula, according to an exemplary embodiment.

According to an exemplary embodiment, a curved cannula may be processed to reduce the surface roughness of an interior surface of the curved cannula. For example, the interior surface of the curved cannula may be polished to reduce its surface roughness. Polishing the interior surface may result in a surface roughness of, for example, about 2 micro-inches to about 4 micro-inches. One exemplary method of polishing an interior surface of a curved cannula is an extrusion honing process, in which a slurry is forced through the interior of a curved cannula. Turning to FIG. 6, an exemplary embodiment of a polishing process is shown for a tube of a cannula 520, which may be straight before at least a portion of cannula 520 is curved or cannula 520 may have at least a curved portion before the polishing process. The polishing process of the exemplary embodiment of FIG. 6 may be an extrusion honing process in which a ram 526, such as, for example, a hydraulic ram, forces a slurry 524 through an interior of cannula 520. Slurry 524, which may include abrasive particles 528, contacts and polishes the interior surface 522 of the cannula 520 as slurry 524 is forced through cannula 520.

Figure 7:
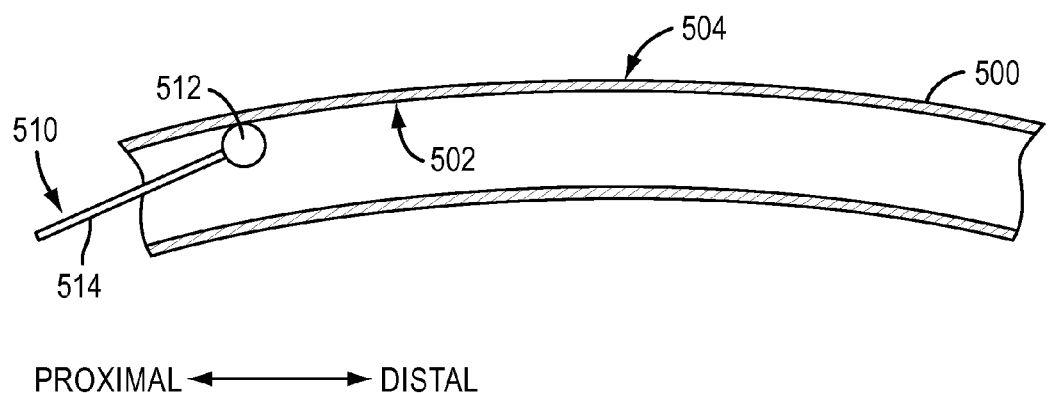
FIG. 7 is a side cross-sectional view of a cannula and burnishing tool inserted within the cannula, according to an exemplary embodiment.

A burnishing step may be performed as an additional step to provide or enhance the galling resistance between the curved cannula and a surgical instrument. Burnishing may be conducted as an additional step to polishing or in lieu of polishing. Turning to FIG. 7, an exemplary embodiment of a burnishing process is shown for a tube of a curved cannula 500. Burnishing a curved cannula 500 may include, for example, pressing a hard material against an inner surface 502 of curved cannula 500. The hard material may have a hardness greater than the hardness of the curved cannula material. As shown in the exemplary embodiment of FIG. 7, the hard material may be in the form of a burnishing tool 510 that includes a sphere 512 of the hard material attached to a shaft 514.

The burnishing tool 510 may be advanced and withdrawn along proximal and distal directions indicated in FIG. 7, or along other directions, while the hard material of sphere 512 is pressed against inner surface 502 of curved cannula 500. As a result, the hard material used to burnish the inner surface 502 of the curved cannula 500 imparts a surface stress that exceeds the yield strength of the curved cannula material, causing localized plastic deformation. Thus, burnishing may include the plastic deformation of the inner surface 502 of the curved cannula tube due to a sliding contact with an object having a hardness greater than the material of the curved cannula tube. Further, burnishing may occur when the contact stress locally exceeds the yield strength of the material used to make the curved cannula tube. According to an exemplary embodiment, burnishing inner surface 502 of a curved cannula 500 may result in inner surface 502 having a greater galling resistance than an outer surface 504 of curved cannula 502. Further, the inner surface may have a surface roughness lower than the outer surface.

The manufacture of a surgical apparatus may include other steps to address the issue of galling. According to an exemplary embodiment, a surgical apparatus may include a lubricant to reduce stress between sliding surfaces of the surgical apparatus. For instance, a friction-reducing material may be applied to at least a portion 406 of the surface of end effector 404 that is likely to contact the curved cannula 410 when the end effector 404 is passed through the interior of the cannula 410. In another instance, the friction-reducing material can be applied to the inner surface of the cannula. The friction-reducing material can be any medically safe lubricant. Rotaglide® lubricant manufactured by Boston Scientific Corporation in Natik, Mass., is an example of commercially available, medically safe lubricant. According to an embodiment, a friction-reducing material may be provided as a coating applied to a surface of an end effector or an inner surface of a curved cannula. An example of such a coating is polytetrafluoroethylene (PTFE), such as TEFLON®, or a coating including diamond-like-carbon (DLC).

According to another exemplary embodiment, the galling resistance of a surgical instrument may be enhanced by enlarging one or more surfaces of an end effector of the surgical instrument to increase the amount of contact area between the end effector and a curved cannula. By doing so, a given load applied between the end effector and the curved cannula is distributed over a larger area, which results in a lower stress applied to the end effector and the curved cannula, which in turn may minimize or avoid galling. According to another exemplary embodiment, the galling resistance of a surgical instrument may be enhanced by selecting a radius of curvature of a contact point or surface of an end effector of the surgical instrument to be close to, or match, a radius of curvature of the curved cannula. For example, a radius curvature at surface 406 of end effector 404 may be close to, or match, a radius of curvature of curved cannula 410 in the exemplary embodiment of FIG. 5. If a radius of curvature of the curved cannula varies, the radius of curvature at the point or surface of the end effector may be close to, or match, smallest radius of curvature of the curved cannula, according to an exemplary embodiment. A radius of curvature at surface 406 of end effector 404 and a radius of curvature of curved cannula 410 in the exemplary embodiment of FIG. 5 may each be about 4 inches to about 6 inches, according to an exemplary embodiment.

In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of a surgical instrument.

For the purposes of this specification and appended claims, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

The terms "proximal" and "distal" are relative terms, where the term "distal" refers to the portion of the object furthest from an operator of the instrument and closest to the surgical site, such as the opening of the tool cover or the end effector of the instrument. The term "proximal" indicates the relative proximity to the operator of the surgical instrument and refers to the portion of the object closest to the operator and farthest from the surgical site. In this application, a distal end effector refers to a device installed at the distal end of an instrument, including but not limited to forceps or graspers, needle drivers, scalpels, scissors, and cauterizing tools.

The term "flexible" in association with a mechanical structure or component should be broadly construed. In essence, the term means the structure or component can be repeatedly bent and restored to an original shape without harm. Many "rigid" objects have a slight inherent resilient "bendiness" due to material properties, although such objects are not considered "flexible" as the term is used herein. A flexible mechanical structure may have infinite degrees of freedom (DOF's). Examples of such structures include closed, bendable tubes (made from, e.g., NITINOL, polymer, soft rubber, and the like), helical coil springs, etc. that can be bent into various simple and compound curves, often without significant cross-sectional deformation. Other flexible mechanical structures may approximate such an infinite-DOF piece by using a series of closely spaced components that are similar to "vertebrae" in a snake-like arrangement. In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible structure may serve as, and be modeled as, a single mechanical constraint (joint) that provides one or more DOF's between two links in a kinematic chain, even though the flexible structure itself may be a kinematic chain made of several coupled links. Knowledgeable persons will understand that a component's flexibility may be expressed in terms of its stiffness.

In this description, a flexible mechanical structure or component may be either actively or passively flexible. An actively flexible piece may be bent by using forces inherently associated with the piece itself. For example, one or more tendons may be routed lengthwise along the piece and offset from the piece's longitudinal axis, so that tension on the one or more tendons causes the piece to bend. Other ways of actively bending an actively flexible piece include, without limitation, the use of pneumatic or hydraulic power, gears, electroactive polymer, and the like. A passively flexible piece is bent by using a force external to the piece. An example of a passively flexible piece with inherent stiffness is a plastic rod or a resilient rubber tube. An actively flexible piece, when not actuated by its inherently associated forces, may be passively flexible. A single component may be made of one or more actively and passively flexible portions in series.

It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical apparatus, comprising:
a cannula including a curved longitudinal axis along at least a portion of the length of the cannula; and
a surgical instrument having an elongated shaft and an end effector, the elongated shaft having a distal end and a proximal end, the end effector being coupled to the distal end of the elongated shaft;
wherein the end effector is configured in a way that results in a portion of the end effector contacting an inner surface of the cannula during insertion of the surgical instrument through the curved cannula; and
wherein the material used for the portion of the end effector and the material used for the inner surface of the curved cannula provide a threshold galling stress between the portion of the end effector and the inner surface of the curved cannula of at least 10,000 pounds per square inch.

2. The surgical apparatus of claim 1, wherein the portion of the end effector comprises an austenitic stainless steel.

3. The surgical apparatus of claim 1, wherein the curved cannula comprises a martensitic stainless steel.

4. The surgical apparatus of claim 3, wherein the martensitic stainless steel is an age-hardenable stainless steel having a composition comprising, in weight percent, about 0.02% maximum carbon, about 0.25% maximum silicon, about 10.75% to about 11.25% nickel, about 1.50% to about 1.80% titanium, about 0.25% maximum manganese, about 11.00% to about 12.50% chromium, about 0.75% to about 1.25% molybdenum, and balance iron.

5. The surgical apparatus of claim 1, wherein the material used for the portion of the end effector and the material used for the inner surface of the curved cannula provide the threshold galling stress between the portion of the end effector and the inner surface of the curved cannula of at least 20,000 pounds per square inch.

6. The surgical apparatus of claim 1, wherein the material used for the portion of the end effector and the material used for the inner surface of the curved cannula provide threshold galling stress between the portion of the end effector and the inner surface of the curved cannula of at least 50,000 pounds per square inch.

7. The surgical apparatus of claim 1, wherein the cannula has a proximal end, a distal end, and a rigid curved section between the proximal end and the distal end.

8. The surgical apparatus of claim 1, wherein the end effector is configured to perform at least one surgical procedure chosen from tissue cutting, tissue grasping, tissue sealing, tissue connection, and tissue ablation.

9. The surgical apparatus of claim 1, wherein the surgical instrument is an instrument configured for use in a teleoperated surgical system.

10. The surgical apparatus of claim 1, wherein the surgical instrument further comprises a force transmission mechanism configured to be operably coupled to a patient side manipulator of a teleoperated surgical system.

11. The surgical apparatus of claim 1:
wherein the curved cannula comprises a tube having the inner surface and an outer surface; and
wherein the inner surface has a wear resistance higher than a wear resistance of the outer surface, a galling resistance higher than a galling resistance of the outer surface, or both a wear resistance higher than a wear resistance of the outer surface and a galling resistance higher than a galling resistance of the outer surface.

12. The surgical apparatus of claim 1, wherein the end effector comprises an austenitic stainless steel having a composition comprising, in weight percent, about 0.15% maximum carbon, about 4% to about 8.5% manganese, about 15% to about 21% chromium, about 4% to about 10% nickel, about 2.5% to about 4.5% silicon, about 0.05% to about 0.25% nitrogen, and balance iron.

* * * * *